United States Patent
Morgan et al.

(10) Patent No.: US 6,205,347 B1
(45) Date of Patent: Mar. 20, 2001

(54) SEPARATE AND COMBINED MULTI-MODALITY DIAGNOSTIC IMAGING SYSTEM

(75) Inventors: Hugh T. Morgan, Highland Heights; Darrell M. Smith, Cleveland Hts.; Carl J. Brunnett, Willoughby Hills, all of OH (US)

(73) Assignee: Picker International, Inc., Highland Heights, OH (US)

( * ) Notice: Subject to any disclaimer, the term of this patent is extended or adjusted under 35 U.S.C. 154(b) by 0 days.

(21) Appl. No.: 09/259,087

(22) Filed: Feb. 26, 1999

Related U.S. Application Data

(60) Provisional application No. 60/076,186, filed on Feb. 27, 1998.

(51) Int. Cl.[7] .................................................. A61N 5/00
(52) U.S. Cl. ............................................................ 600/407
(58) Field of Search .................................... 600/407, 411, 600/415, 425, 427; 128/906

(56) References Cited

U.S. PATENT DOCUMENTS

| | | |
|---|---|---|
| 5,391,877 | 2/1995 | Marks. |
| 5,485,839 * | 1/1996 | Aida et al. ............................ 600/527 |

OTHER PUBLICATIONS

"Investigation of the Use of X–Ray CT Images for Attenuation Compensation in SPECT", K.J. LaCroix et al. IEEE Transactions on Nuclear Science, vol. 41, No. 6, Dec., 1994.
"Object–Specific Attenuation Correction of SPECT with Correlated Dual–Energy X–Ray CT", Bruce H. Hasegawa et al. IEEE Transactions on Nuclear Science, vol. 40, No. 4, Aug., 1993.

* cited by examiner

Primary Examiner—William E. Kamm
(74) Attorney, Agent, or Firm—Fay, Sharpe, Fagan, Minnich & McKee, LLP

(57) ABSTRACT

A multi-modality diagnostic imaging system includes a first imaging subsystem (A), such as a computed tomographic (CT) system, for performing a first imaging procedure on a subject. A second imaging subsystem (B), such as a nuclear medicine system (NUC), performs a second imaging procedure on a subject. The second imaging subsystem (B) is remote from the first imaging system (A). A patient couch (28) supports a subject. A patient transfer subsystem (C) transfers a patient couch (28) between the first imaging subsystem (A) and the second imaging subsystem (B). The first and second imaging subsystems (A, B) can be operated concurrently to perform different imaging procedures on different subjects supported by separate patient couches. Data generated by the first imaging subsystem (A) can be used to correct emission data generated by the second imaging subsystem (B).

26 Claims, 2 Drawing Sheets

SEPARATE AND COMBINED MULTI-MODALITY DIAGNOSTIC IMAGING SYSTEM

CROSS REFERENCE TO RELATED APPLICATIONS

This application claims the benefit of U.S. Provisional Patent Application Ser. No. 60/076,186, filed Feb. 27, 1998.

BACKGROUND OF THE INVENTION

The present invention relates to the art of diagnostic imaging. It finds particular application in conjunction with a separate and combined multi-modality diagnostic imaging system, and more particularly, a separate and combined computed tomographic/nuclear medicine (CT/NUC) diagnostic imaging system. It should be appreciated, however, that the present invention may find application with imaging modalities other than computed tomography (CT) and/or nuclear medicine (NUC).

Nuclear medicine imaging, such as single photon emission computed tomography (SPECT), is used to study radionuclide distribution in subjects. Typically, one or more radiopharmaceuticals are injected into a subject. The radiopharmaceuticals are commonly injected into the subject's blood stream for imaging the circulatory system or for imaging specific organs which absorb the injected radiopharmaceuticals. One or more gamma or scintillation camera heads are placed closely adjacent to a surface of the subject to monitor and record emitted radiation.

In single photon-emission computed tomography, the camera head(s) is rotated slowly or indexed around the subject to monitor the emitted radiation from a plurality of directions. The radiation data from the multiplicity of directions monitored over several minutes, e.g. 10–20 minutes, is reconstructed into a three dimensional image representation of the radiopharmaceutical distribution within the subject.

In computed tomographic (CT) diagnostic imaging, a thin fan-shaped beam of radiation is projected from an x-ray source through a region of interest. The radiation source is rotated rapidly about the region of interest such that the same thin slice of the region of interest is irradiated from a multiplicity of directions spanning 360°. For a volumetric image representation, the source rotates at speeds on the order of 1 sec/revolution or less while the patient is moved longitudinally to irradiate the patient along a spiral path.

Typically, computed tomographic (CT) imaging systems and nuclear medicine imaging systems are located in separate imaging suites with no physical and/or functional connections therebetween. The diagnostic images that result from the respective imaging studies can be viewed concurrently on adjoining screens for diagnostic purposes. However, the value of these image combinations and comparisons is compromised by having been obtained in separate study episodes. These separate study episodes are performed at different locations between which the patient typically walks. Repositioning the patient in the same position is imprecise. The episodes are usually separated by significant Lime intervals (days or even weeks) after which significant functional and anatomical changes can occur in addition to the repositioning problem. These separate study episodes are also performed by different medical personnel which distracts from the comparative value of the separate images.

U.S. Pat. No. 5,391,877 describes a dedicated combined diagnostic, imaging device that fuses together data obtained by a computed tomographic (CT) scanner and a single photon emission computed tomographic scanner (SPECT) to yield a color shaded relief image. The combined diagnostic imaging device includes combined gantries supporting both of the CT and SPECT scanners, a computer, a printer, and a table top that passes through both gantries while holding a patient in a fixed position.

However, the combined diagnostic imaging device described in the '877 patent requires an inefficient use of dedicated imaging hardware and patient care personnel. That is, the CT detectors and CT gantry sit idle most of the time waiting for the temporally longer nuclear study to complete.

Accordingly, it has been considered desirable to develop a new and improved separate and combined multi-modality diagnostic imaging system which meets the above-stated needs and overcomes the foregoing difficulties and others while providing better and more advantageous results.

SUMMARY OF THE INVENTION

In accordance with one aspect of the present invention, a multi-modality diagnostic imaging system is disclosed. The multi-modality diagnostic imaging system includes a first imaging subsystem for performing a first imaging procedure on a subject. A second imaging subsystem performs a second imaging procedure on a subject, the second imaging subsystem being remote from the first imaging system. A patient couch adapted for supporting a subject. A patient transfer subsystem transfers the patient couch between the first imaging subsystem and the second imaging subsystem.

In accordance with another aspect of the present invention, a diagnostic imaging suite is disclosed. The diagnostic imaging suite includes a first imaging system positioned within the imaging suite for performing a first imaging procedure on a subject supported on a patient couch. A second imaging system is positioned within the imaging suite remote from the first imaging system and performs a second imaging procedure on a subject supported on a patient couch, the second imaging procedure taking a plurality of times longer than the first imaging procedure. A patient transfer system transfers patient couches and the supported subjects between the first imaging system and the second imaging system. A control and processing system includes a first reconstruction processor for generating image representations from data generated by the first imaging system. A second reconstruction processor generates image representations from data generated by the second imaging system. A mechanism combines the image representations generated by the first and second imaging systems into combined image representations. At least one monitor displays at least one of a first image representation of a first subject generated by the first imaging system, a second image representation of a second subject generated by the second imaging system, and a third combined image representation of the first subject generated by both the first imaging system and the second imaging system.

In accordance with another aspect of the present invention, a method of performing a diagnostic imaging procedure is disclosed. The method includes a) positioning a subject on a patient table; b) performing a first imaging procedure on the subject using a first imaging system; c) transferring the patient table to a second imaging system; d) performing a second imaging procedure on the subject; e) generating a first image representation from data generated by the first imaging system; f) generating a second image representation from data generated by the second imaging system; g) combining the data representing first image representation and the data representing the second image representation into a combined image representation; and h) displaying at least one of the first image representation, the second image representation, and the combined image representation on at least one video monitor.

One advantage of the present invention is the provision of a new and improved separate and combined multi-modality diagnostic imaging system that provides CT anatomical imaging with nuclear medicine functional imaging in one clinical study episode (location and time period) and in such a manner that clinical productivity and patient care are improved.

Another advantage of the present invention is the provision of a new and improved separate and combined multi-modality diagnostic imaging system that generates multi-modality imaging data for attenuation correction, tumor localization, and image fusion. The CT imaging system provides a means for fast and accurate attenuation correction of the nuclear images, removing a major weakness of current SPECT/PCD and PET nuclear imaging systems.

Yet another advantage of the present invention is the provision of a new and improved separate and combined multi-modality diagnostic imaging system where a patient is imaged on the exact same table, and in a single imaging episode. This permits the subject to be in the same external and internal imaging states during both imaging studies.

Still another advantage of the present invention is the provision of a new and improved separate and combined multi-modality diagnostic imaging system that combines functional images (i.e. nuclear) with anatomical images (i.e. CT) via image fusion and side by side image registration Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment(s) and are not to be construed as limiting the invention.

DETAILED DESCRIPTION OF THE PREFERRED EMBODIMENT(S)

Figure 1:
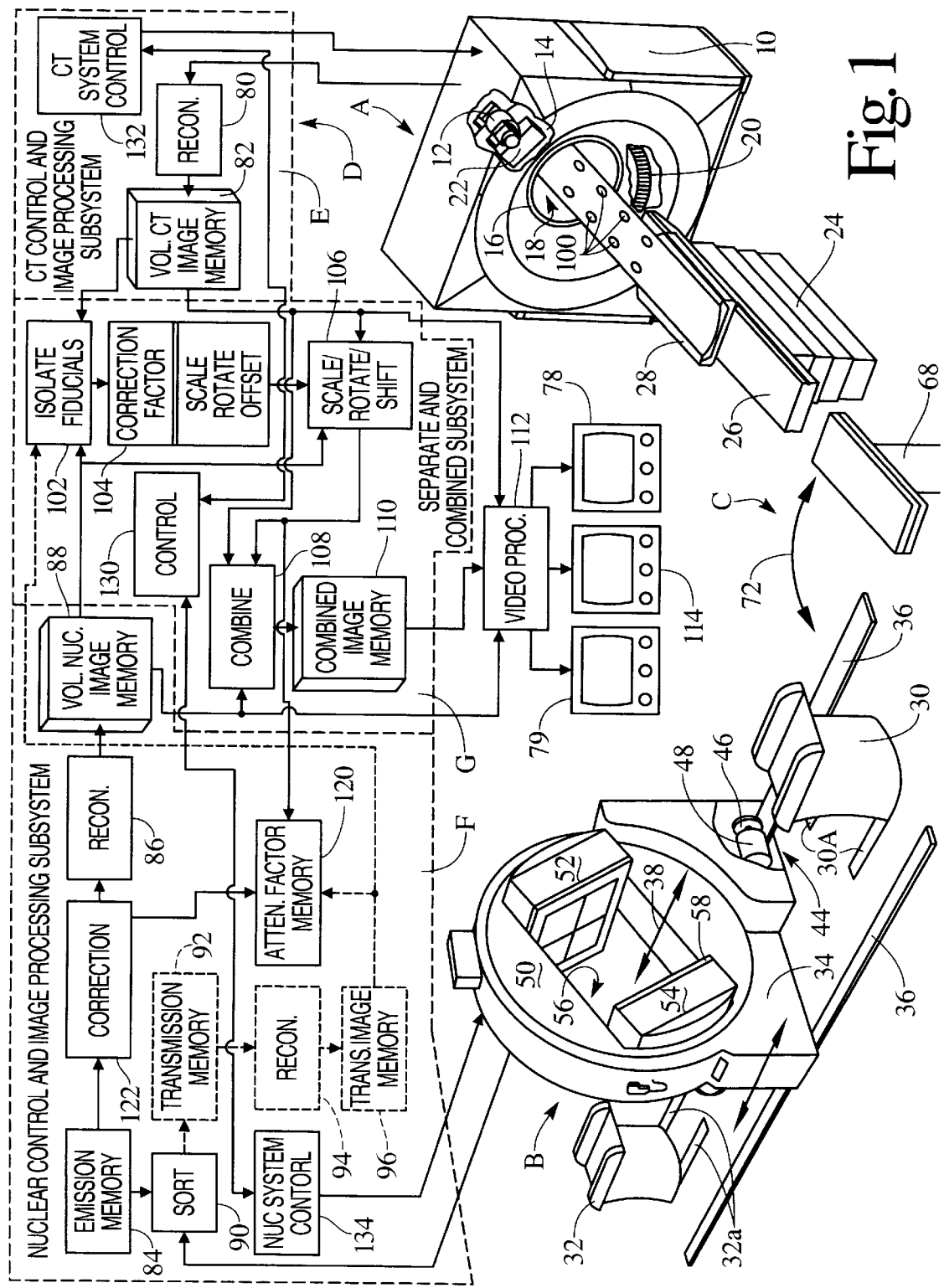
FIG. 1 is a perspective view of a separate and combined multi-modality diagnostic imaging system that incorporates a computed tomographic (CT) scanner system and nuclear medicine (NUC) system in accordance with the present invention.
Figure 2:
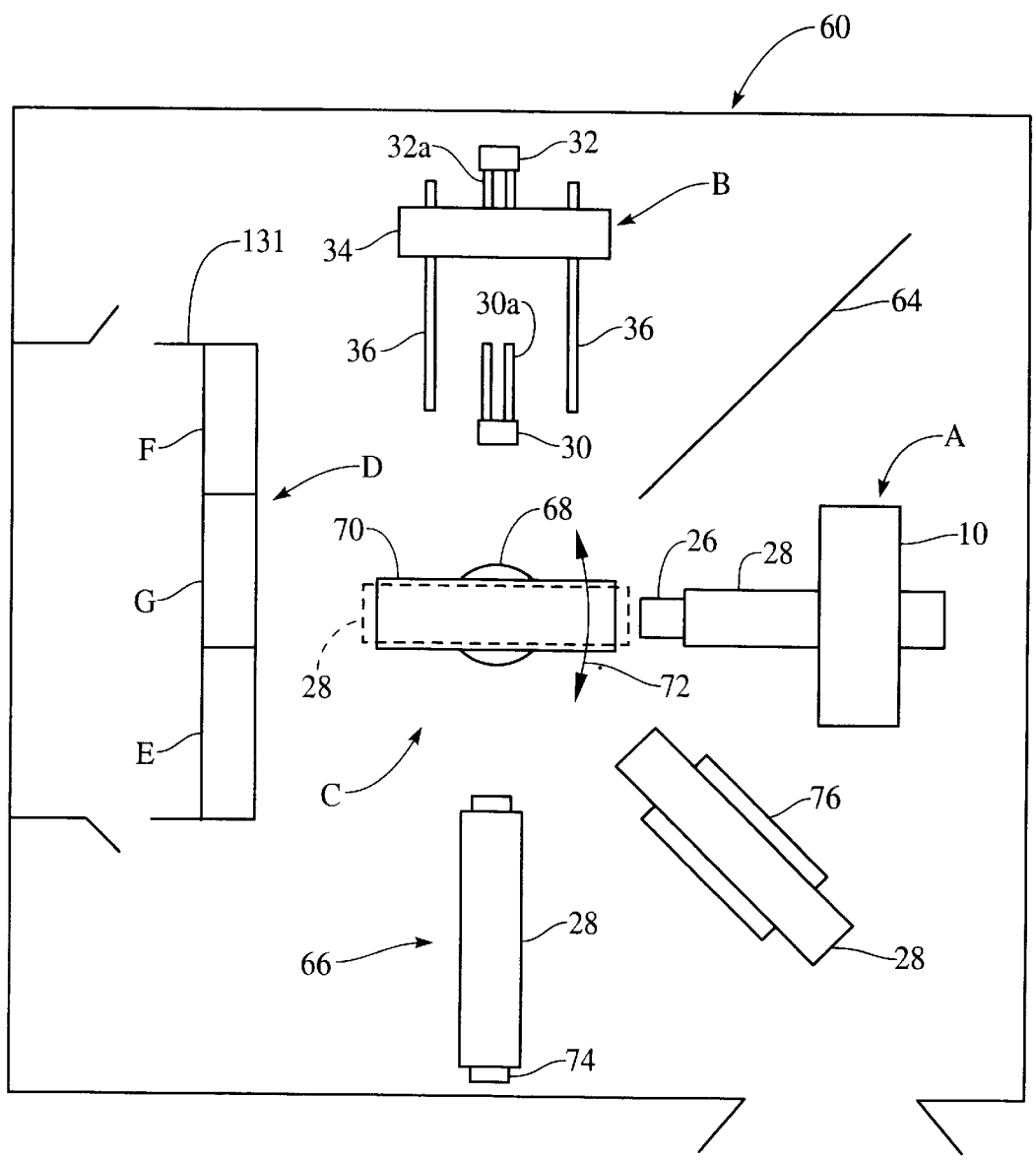
FIG. 2 is a plan view of a diagnostic imaging suite for housing the separate and combined multi-modality diagnostic imaging system of FIG. 1.

With reference to FIGS. 1 and 2, a separate and combined multi-modality diagnostic imaging system of the present invention includes a computed tomographic (CT) scanner A includes a floor-mounted, non-rotating gantry 10 whose position remains fixed during data collection. An x-ray tube 12 is rotatably mounted on a rotating gantry 14. The stationary gantry 10 includes a cylinder 16 that defines a patient examination region 18. An array of radiation detectors 20 are disposed concentrically around the patient receiving region. In the illustrated embodiment, the x-ray detectors are mounted on the stationary gantry portion such that an arc segment of the detectors receives radiation from the x-ray tube 12 which has traversed the examination region 18. Alternatively, an arc segment of radiation detectors can be mounted to the rotating gantry 14 to rotate with the x-ray tube 12.

The x-ray tube 12 includes an oil filled housing that has an x-ray permeable window directed toward the patient receiving region. An evacuated envelope is disposed within the housing and contains a rotating anode, such as a 7-inch anode, and a cathode or other electron source. High voltages, on the order of 100 kV and higher applied between the rotating anode and the cathode, cause the generation of x-rays. The x-rays pass through the x-ray permeable window and across the patient receiving region 18. Appropriate x-ray collimators 22 focus the radiation into one or more planar beams which span the examination region 18, as is conventional in the art.

A stationary support 24 is positioned adjacent the CT gantry 10 so as to extend from the examination region 18 in a first direction substantially along a central axis of the cylinder 16. A beam 26 is secured to the support 24. A removable patient couch or table 28 is adapted for back and forth movement through the examination region 12 along the beam 26. The CT system includes conventional pilot, axial, and spiral scanning and imaging capability.

The separate and combined multi-modality diagnostic imaging system of the present invention also includes a nuclear medicine imaging system (NUC) B. The nuclear medicine imaging system B includes a first patient table support 30 and a second patient table support 32 respectively positioned on opposing sides of an outer gantry structure 34. The outer gantry structure is mounted on tracks 36 that extend parallel to a longitudinal axis 38. This enables the outer gantry structure to be moved parallel to the longitudinal axis 38.

An outer gantry structure moving means 44 is provided for selectively moving the outer gantry structure 34 along the rails 36 in a path parallel to the longitudinal axis. In the illustrated embodiment, the longitudinal moving means includes drive wheels 46 for supporting the outer gantry structure on the tracks. A motive power source, such as a motor 48, selectively drives one of the wheels which frictionally engages the track and drives the outer gantry structure and a supported inner gantry structure and detector heads therealong. Alternately, the outer gantry can be stationary and the patient table supports 30, 32 can be configured to move the patient table 28 along the longitudinal axis 38.

An inner gantry structure 50 is rotatably mounted on the outer gantry structure 34. A first camera or detector head 52 is movably mounted to the inner gantry structure. A second detector head 54 is movably mounted to the inner gantry structure opposite to the first camera head. The detector heads are independently movable toward and away from each other. The inner gantry structure defines a central, subject receiving aperture 56 for receiving the subject patient table and, particularly along the longitudinal axis. The aperture 56 is enlarged to receive the detector heads in any of a variety of displacements from a central axis and angular orientations. The patient table supports 30, 32 can be adapted to move the patient table 28 up and/or down to position the subject in the center of the subject receiving aperture 56.

The detector heads 52, 54 can have collimators 58 removably mounted on a front face to restrict received radiation to radiation traveling generally perpendicular to the face. The face includes a scintillation crystal that emits a flash of light in response to incident radiation. An array of photomultiplier tubes convert the light into electrical signals. A resolver circuit resolves the x, y-coordinates of each light flash and the energy of the incident radiation.

Either one or both of the patient table supports 30, 32 can be movably mounted on respective tracks 30$a$, 32$a$ for movement in directions along the longitudinal axis 38. The patient table supports 30, 32 cooperate to receive and support a removable patient table 28 during operation of the imaging system B as described in more detail below.

It should be appreciated that the nuclear medicine imaging system B could incorporate either a SPECT/PCD (Positron Co-incidence Detection) scintillation detector and acquisition system, or a dedicated conventional PET (Positron Emission Tomography) detector and acquisition system. In the embodiment being described, the nuclear medicine imaging system B includes a SPECT/PCD gamma camera system having an opposed dual head camera with large field of view (LFOV) detectors (i.e. 40 cm×50 cm FOV). The nuclear medicine imaging system B can be operated in any one of the conventional Planar, Planar Whole Body, and SPECT/PCD acquisition and imaging modes.

With continuing reference to FIG. 2, there is shown a plan view of a diagnostic imaging suite 60 for housing the separate and combined multi-modality diagnostic imaging system. In addition to the CT imaging system A and 20 the nuclear medicine imaging system B, the separate and combined multi-modality diagnostic imaging system further includes a table transfer system C and a separate and combined control and image processing system D.

The separate and combined control and image processing system D controls the table top/patient transfer system C and provides separate and combined image processing and display of i) CT data and studies, ii) NUC data and studies, and iii) combined CT/NUC data and studies. It should be appreciated that combining CT and SPECT/PCD images provides for more precise localization of tumor and tumor borders for prognosis, biopsy, therapy and surgery. The combined control and processing system D also provides image reconstructions, image registrations, nuclear non-uniform attenuation correction, and advanced combined image display functions. As described further below, accurate attenuation correction of the nuclear images can be accomplished by properly scaling the CT images for energy differences. Air, lung, soft tissue and bone can be scaled separately as a function of energy to achieve accurate and quantative nuclear images.

In the embodiment being described, the CT scanner and nuclear medicine imaging system B are located within the same imaging suite 60 and are separated by one or more radiation barriers 64. The table transfer system C provides means for transferring independently movable patient tables 28 between the CT scanner A, the nuclear medicine imaging system B, and a patient table queuing station 66.

The table transfer system C includes a base 68 and rail 70 secured to the base 68 that is adapted for receiving a movable patient table. The base 68 and/or the rail 70 is pivotal or otherwise rotatable in the directions shown by arrow 72. In addition, the height of the base 68 and/or rail 70 may be raised and lowered to facilitate transferring a movable patient table to and from the CT scanner A, the nuclear medicine imaging system B, etc.

In the described embodiment, the CT scanner A is offset from the nuclear medicine imaging system B by about 90°, and the patient table queuing station 66 is offset from the nuclear medicine imaging system B by about 180°, with the pivotal base 68 centrally positioned therebetween. The table queuing station 66 includes a base (not shown) and a rail 74 mounted to the base that is adapted for supporting a movable patient table. A movable patient table can be transferred to and from the rail 70 (or any of the other rails or supports 26, 30, 32, 74) via a wheeled gurney 76 that is adapted for supporting a patient table.

In preparation for a diagnostic imaging procedure, a patient can be positioned on and secured to a patient table 28 that is supported on any one of the rails or supports 26, 30, 32, 74, or on the gurney 76. In the case where the patient table is supported on the gurney 76, the base 68 and/or the rail 70 can be rotated into axial alignment with the gurney 76 to facilitate transferring the patient table from the gurney 76 to the rail 70. For instance, as shown in FIG. 2, the base 68 and/or rail 70 would be manually or automatically rotated about 45° in a clockwise direction to receive the patient table. The gurney and/or the patient table may include interlocks securing the table to the gurney, and such interlocks can be manually or automatically released prior to transferring the patient table to the rail 70. Further, the gurney and/or the rail 70 may include manual or automatic alignment means for aligning the gurney and/or the patient table with the base 68 and/or the rail 70 to insure reliable transfer of the patient table to the rail 70.

Once aligned, the patient table can then be manually or automatically driven (pushed or pulled) on to the rail 70 from the gurney. The rail 70 and/or the patient table may include interlocks securing the table to the rail 70, and such interlocks can be manually or automatically engaged after transferring the patient table to the rail 70. With the patient table transferred and locked to the rail 70, the base 68 and/or rail 70 can be manually and/or electrically driven (i.e. rotated) into alignment with either of the CT scanner A or the nuclear medicine imaging system B. Mechanical and/or electric alignment means may be provided for aligning the rail 70 and/or the patient table with the respective rail 26, or supports 30, 32 to insure reliable transfer of the patient table to the respective imaging system A, B. The patient table can then be manually or automatically driven (pushed or pulled) on and off the designated rail 26, or supports 30, 32 from the rail 70. The rail 26, or supports 30, 32 and/or the patient table may include interlocks for slidably and/or fixedly securing the table to the respective rail 26, or supports 30, 32. Such interlocks can be manually or automatically engaged after transferring the patient table to the respective rail 26, or supports 30, 32.

It is contemplated that the patient table can be temporarily transferred from the rail 70 to the queuing station 66 in the event that the designated imaging system A, B is in use. When the designated imaging system A, B becomes available, the patient table can be transferred back to the rail 70 and then transferred to the designated rail 26, or supports 30, 32 in the same manner described above. The patient table can be manually or automatically driven (pushed or pulled) on and off the rail 74. The rail 74 and/or the patient table may include interlocks for slidably and/or fixedly securing the table to the rail 74. Such interlocks can be manually or automatically engaged after transferring the patient table to the rail 74.

Assuming that a table supporting a subject has been transferred to the rail 26 associated with the CT imaging system A. The patient table can be driven along the rail 26 so as to position the subject within the examination region 18 of the gantry 10. The CT imaging system A can be separately controlled by the separate and combined control and image processing system D. The separate and combined control and image processing system D includes a CT control and image processing subsystem E for reconstructing CT image representations in a known manner. That is, the CT control and image processing subsystem E reconstructs a volumetric image representation from radiation attenuation data taken by the CT scanner along a spiral path through the patient. In spiral scanning techniques, the patient is generally moved continuously through the x-ray beam as the x-ray source rotates around the region of interest. In this manner, the fan shaped beam of radiation and the region of interest move in a spiral pattern relative to each other.

The CT control and image processing subsystem E converts selectable portions of the reconstructed images representations into a two-dimensional human-readable image representation for display on a dedicated video monitor 78. The CT control and image processing subsystem E can include known tape and disk recording devices for archiving image representations, and can also include known circuitry for performing image enhancements, selecting planes, 3D renderings, or color enhancements, and the like. Various scanner control functions such as initiating a scan, selecting among different types of scans, calibrating the 15 system, and the like, are also performed by the CT control and image processing subsystem E.

An initial patient diagnosis, based on the results of a CT study obtained with the CT imaging system A, may suggest that a follow-up nuclear medicine imaging be performed. In such a case, the movable patient table 28 (and patient secured thereto) is transferred directly from the CT imaging system A to the nuclear imaging system B via the patient transfer system C. In particular, with the patient table transferred and locked to the rail 70, the base 68 and/or rail 70 can be manually and/or electrically driven (i.e. rotated) into alignment with the nuclear medicine imaging system B. The patient table can then be manually or automatically driven (pushed or pulled) on to the supports 30, 32 from the rail 70.

As mentioned, the supports 30, 32 and/or the patient table may include interlock means such as rails or mutually conforming interengaging members (i.e. dovetail connections) for slidably and/or fixedly securing the table to the respective supports 30, 32. Such interlocks can be manually or automatically engaged during and after transferring the patient table to the respective supports 30, 32. Either one or both of the supports 30, 32 can be manually or automatically driven along the respective rails 30a, 32a to facilitate receiving the patient table 28 from the rail 70. The patient table will cantilever as it passes from the rail 70 to the support 30 and as it passes from the support 30 through the aperture 56 of the inner gantry 50. A free end of the patient table engages the support 32 after the free end has passed through the aperture 56. Thus, the patient table is supported at both ends thereof by the respective supports 30, 32 during operation of the imaging system B.

While the temporally longer nuclear study is taking place, the CT system A can be scanning a second patient using a second system table top. If the second patient does not require a nuclear scan for diagnosis, then a CT scan can be performed on a third patient while the first patient is finishing-up on the nuclear gantry. Thus, the CT Scanner can continue to be utilized while the longer nuclear scan is taking place. In the event that a nuclear study is in progress, a patient table can be temporarily transferred from the CT imaging system A to the queuing station 66 and/or a gurney 76 until the nuclear imaging system B is available.

Assuming that a table supporting a subject has been transferred to the support 30 associated with the nuclear imaging system B. The gantry 34 can be driven along the rails 36 to position the examination region 56 at a predetermined location along the rails 34 and/or patient table 28. The nuclear imaging system B can be separately controlled by the separate and combined control and image processing system D. As described further below, the separate and combined control and image processing system D includes a NUC control and image processing subsystem F that reconstructs nuclear emission data into diagnostic image representations for display on a dedicated video monitor 79 in a known manner. It should be appreciated that reconstruction techniques change according to the types of radiation collected and the types of collimators used (i.e., fan, cone, parallel beam). Emission radiation from the subject is received by both detector heads 52 and 54 and emission projection data is generated. The emission data normally contains inaccuracies caused by varying absorption characteristics of the subject's anatomy.

That is, one of the problems with the SPECT imaging is that the patient is not completely homogeneous in terms of radiation attenuation or scatter. Rather, the human patient includes many different tissue and bone types which absorb or scatter radiation from the radiopharmaceuticals to different degrees. The SPECT images can be made more accurate if they are corrected for the radiation lost to scattering or attenuation along each path through the human torso. One approach is to provide a point or line source of transmitted radiation to correct for the radiation lost to scattering or attenuation.

With reference again to FIG. 1, data from the detectors 20 of the CT scanner A are reconstructed by a reconstruction processor 80 and loaded into a volume CT image memory 82 associated with the CT control and image processing subsystem E. Preferably, the patient table 28 is driven longitudinally as the x-ray tube rotates in order to generate the spiral CT data using conventional spiral CT reconstruction algorithms. When the CT imaging system A is operated independently or separately, CT diagnostic images can be displayed on the video monitor 78 vis-a-vis a video processor 112.

Analogously, the emission radiation data detected by the nuclear camera detector heads 52, 54 is transferred to an emission data memory 84 and reconstructed by a reconstruction processor 86 and stored in a volume nuclear image memory 88 associated with the NUC control and image processing subsystem F. When the NUC imaging system B is operated independently or separately, nuclear diagnostic images can be displayed on the video monitor 79 vis-a-vis the video processor 112. Commonly, a transmission radiation source is mounted to one of the detector heads 52, 54 to generate transmission radiation which is received by the other detector head. When such a transmission radiation source is present, a sorting circuit 90 sorts the transmission and emission radiation based on energy levels. The transmission radiation is conveyed to a transmission radiation data memory 92. A reconstruction processor 94 reconstructs the transmission data into a volumetric image representation which is stored in a transmission image memory 96.

The patient is secured to the patient couch 28 and remains substantially immobile during both the CT and nuclear camera scans. Preferably, the patient table includes a series of fiducials or markers 100 disposed or mounted at known locations along the table top to aid in the registration of the resulting CT and nuclear images. The markers can be imbedded within the table material or can be attached to the table in a fixed and stable manner. Optionally, fiducials can also be affixed to the patient.

The fiducials are constructed of a material(s) that is opaque to x-rays and that emits radiation in an energy band that is detected by the detector heads 52, 54. More particularly, the fiducials include radio nuclide point sources surrounded by or contained within a plastic sphere. The radio nuclide sources are visible in the resulting images and serve as an aid in accurate image registration and fusion, and as an aid in verification of accurate registration and fusion.

However, the markers are preferably designed to have relatively weak source strengths and intermediate attenuation factors so that they image in the background but do not introduce artifacts or otherwise interfere with the image quality of the CT or the nuclear images. Thus, the markers can be refillable and thus filled when needed with relatively short lived radio nuclides such as Tc-99m, F-18, etc. Alternatively, the markers can be more permanent and contain longer lived radio nuclides such as Co-57, Gd-153, Ge-68, etc. Preferably, the fiducials include a further identification of individual Fiducials.

The separate and combined control and image processing system D further includes a separate and combined image processing subsystem G. The separate and combined image processing subsystem G is adapted to receive volume nuclear images from the volume nuclear image memory 88 and volume CT images from the volume CT image memory 82 to generate combined or fused diagnostic images as described further below.

In particular, the separate and combined image processing subsystem G includes a fiducial isolating circuit 102 identifies the fiducials in the CT and nuclear images. A fiducial isolating circuit 102 isolates the fiducials from the volume CT and nuclear images. A correction factor generating circuit 104 compares the nuclear and CT images of the fiducials. The correction factor determines a scaling factor, one or more rotation factors, and the like which bring the CT and nuclear fiducial images into superimposition. A scaling and rotating circuit 106 operates on one of the nuclear and CT volume images with the determined correction factors to bring both volume images into the same scale or magnification and the same viewing angle.

A combining circuit 108 combines the scaled and rotated nuclear and CT images to generate a combined Image which is stored in a combined image memory 110. Optionally, the two images may be color coded, or the like to distinguish the CT and nuclear contributions to the combined image. The video processor 112 converts data from the combined image memory 110 into an appropriate format for display on a combined video monitor 114. Further, the video processor 112 converts data from one or both of the volume nuclear image memory 88 and the volume CT image memory 82 into appropriate formats for display on the video monitors 78, 79. Typical representations might include slice images through the volume, opaque slices, surface renderings, and the like.

In nuclear imaging, radiation is emitted from various points in the interior of the patient's body must pass through tissue between the emission point and the detector head. Some tissue, such as bone attenuates the radiation data significantly more than other tissue, such as soft tissue. Accordingly, the emission data is commonly corrected for the greater attenuation attributable to some intravening tissue relative to others. To this end, one or both of the data from the transmission image memory 96 and the scaled and rotated CT image data are conveyed to an attenuation factor memory 120. Based on one or both of these transmission radiation constructed images, the tissue along the trajectory followed by each emission radiation data value collected is determined at an appropriate attenuation correction factor selected. An emission data correction processor 122 corrects the emission radiation data in accordance with the determined attenuation factor corrections.

Other techniques for aligning the nuclear and CT images are also contemplated. For example, corresponding slices or other portions of the transmission image from the transmission image memory 96 and images from the volume CT image memory 82 can be selected and conveyed to the matching circuit 102. Rather than matching the position of the fiducials, the circuit 102 can use known image matching techniques to match the corresponding image portions, again choosing appropriate scaling, rotation, or offset, or other correction factors to bring the two into superimposition.

The separate and combined image processing subsystem G also includes a workstation controller 130 that controls the transfer of movable patient tables 28 between the imaging systems A and B, the queuing station 66 and the patient transfer system C in response to commands received from a workstation control console 131. The controller 130 also controls the operation of each of the imaging systems A, B via a dedicated CT system controller 132 and a dedicated nuclear system controller 134. Further, the controller 130 also controls the operation of separate and combined image processing subsystem G so as to generate the combined diagnostic images in the manner described above.

The separate and combined CT/NUC imaging system of the present invention is more productive and efficient than the dedicated combined CT/NUC imaging system discussed in the prior art because both imaging modalities (e.g. CT and NUC) can be used simultaneously on separate patients. In other words, the CT imaging system can be used to image other patients while the slower NUC imaging system continues to image the first patient.

In separate imaging episodes, body organs and tissue can move with respect to body bones over relatively short time intervals. Surgery and other trauma events are known to move anatomy within the body. Even subtle things such as the movement of gas, foods and liquids through the body can cause a relative shifting of the body's organs and tissues with respect to the body's frame—those shifts in position can confound accurate registration and fusion of multi-modality images. Also, different external conditions such as tables, table pads, sheets, patient clothing, etc. can cause significant problems with accurate image registration of multi-modality data sets. The subject system is designed to eliminate or at least minimize these confounding factors to accurate multi-modality image registration and fusion.

Thus, data and images acquired on the same table and in the same clinical room and environment and nearly at the same time (i.e. within about 30 minutes), are more valuable than comparable multi-modality images acquired at different times, and in a different imaging environment. The different imaging environment is intended to include the same patient in a different internal imaging state including position of organs, weight, disease or health state, etc. as well as a different external environment state including orientation, posture, clothes, table pads, sheets, room temperature, etc.

The invention has been described with reference to the preferred embodiment(s). Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment(s), the invention is now claimed to be:

1. A multi-modality diagnostic imaging system comprising:
   a first imaging subsystem for performing a first imaging procedure on a subject;
   a second imaging subsystem for performing a second imaging procedure on a subject, the second imaging subsystem being remote from the first imaging system;
   a patient couch adapted for supporting a subject;
   a patient transfer subsystem for transferring the patient couch between the first imaging subsystem and the second imaging subsystem.

2. The imaging system of claim 1, wherein the first imaging subsystem includes:
   a first gantry defining a first patient examination region;
   a first couch support proximate the first examination region and adapted to support the patient couch, the patient couch being movable along the first couch support to position the patient couch at a predetermined location along the first couch support.

3. The imaging system of claim 2, wherein the second imaging subsystem includes:
   a second gantry defining a second patient examination region;
   a second couch support, proximate the second examination region and adapted to support the patient couch, the patient couch being movable along the second couch support to position the patient couch at a predetermined location along the second couch support.

4. The imaging system of claim 3, wherein the patient transfer subsystem includes:
   a base; and
   a third couch support mounted on the base and adapted to support the patient couch, the patient couch being movable along the third coach support, and at least one of the base and the third couch support being movable to move the third couch support between alignment with the first couch support and alignment with the second couch support.

5. The imaging system of claim 4, further including:
   a patient queuing station remote from the first imaging subsystem and the second imaging subsystem, the patient queuing station adapted to support the patient couch, the patient transfer subsystem being selectively alignable with the patient queuing station to transfer the patient couch therebetween.

6. The imaging system of claim 5 further including a plurality of patient couches to facilitate moving a plurality of patients among the first imaging subsystem, the second imaging subsystem, and the queuing station.

7. The imaging system of claim 4, further comprising a control and processing subsystem including:
   a first control and image processing subsystem for reconstructing a first image representation from data generated by the first diagnostic imaging subsystem;
   a second control and image processing subsystem for reconstructing a second image representation from data generated by the second diagnostic imaging subsystem; and
   a combined control and image processing subsystem for combining the first image representation and the second image representation into a combined image representation.

8. The imaging system of claim 7, wherein:
   the patient couch includes at least one fiducial capable of being imaged by both the first imaging subsystem and the second imaging subsystem; and
   the image combining circuit includes a means for combining the data representing first image representation and the data representing the second image representation into the combined image representation based on the at least one imaged fiducial.

9. The imaging system of claim 7 wherein the control and processing subsystem includes:
   a processor for comparing corresponding identifiable elements of the first and second image representations and for determining corrections necessary to bring the identifiable elements of the first and second image representations into alignment; and
   an image adjustment processor for adjusting at least one of the first and second image representations such that the corresponding identifiable elements in the combined image representation are substantially superimposed.

10. The imaging system of claim 7, wherein the control and processing subsystem further includes:
    a means for correcting the data that the second reconstruction processor reconstructs into the second image representation based on the first image representation.

11. The imaging system of claim 7, wherein the control and processing subsystem further includes:
    a means for simultaneously operating the first imaging subsystem and the second imaging subsystem to perform imaging procedures on different subjects supported by separate patient couches.

12. The imaging system of claim 1, wherein the first imaging subsystem includes a computed tomographic (CT) imaging system and the second imaging subsystem includes a nuclear medicine imaging system.

13. A diagnostic imaging suite comprising:
    a first imaging system positioned within the imaging suite for performing a first imaging procedure on a subject supported on a patient couch;
    a second imaging system positioned within the imaging suite remote from the first imaging system for performing a second imaging procedure on a subject supported on a patient couch, the second imaging procedure taking a plurality of times longer than the first imaging procedure;
    a patient transfer system for transferring patient couches and the supported subjects between the first imaging system and the second imaging system;
    a control and processing system including:
    a first reconstruction processor for generating image representations from data generated by the first imaging system,
    a second reconstruction processor for generating image representations from data generated by the second imaging system,
    a means for combining the image representations generated by the first and second imaging systems into combined image representations; and
    at least one monitor for displaying at least one of a first image representation of a first subject generated by the first imaging system, a second image representation of a second subject generated by the second imaging system, and a third combined image representation of the first subject generated by both the first imaging system and the second imaging system.

14. The imaging suite of claim 13, wherein:
    the patient couches include a plurality of markers that are imaged by both the first imaging system and the second imaging system; and the control and processing system includes a means for translating, scaling, and rotating at least one of the first image representation and the second image representation such that corresponding markers are superimposed in a combined image representation.

15. The imaging suite of claim 13, wherein the control and processing system includes:

a means for correcting the second image representation based on the first image representation.

16. The imaging suite of claim 13 wherein the control and processing includes:

a processor for comparing corresponding identifiable elements of the first and second image representations and for determining corrections necessary to bring the identifiable elements of the first and second image representations into alignment; and an image adjustment processor for adjusting at least one of the first and second image representations such that the corresponding identifiable elements in a combined image representation are substantially superimposed.

17. The imaging suite of claim 13, wherein the first imaging system includes a computed tomographic (CT) imaging system and the second imaging system includes a nuclear medicine imaging system.

18. The imaging suite of claim 13, further including a patient queuing station positioned within the imaging suite remote from the first imaging system and the second imaging system, the patient queuing station being adapted to support a patient couch received from the patient transfer system.

19. The imaging suite of claim 13 wherein the patient transfer system includes:

a translating member along which a patient couch is horizontally translated; and a base for moving the translating member into alignment with (i) a first imaging system transfer member along which a patient couch translates to position the subject for the first imaging procedure, and (ii) a second imaging system transfer member along which a patient couch translates to position the subject for the second imaging procedure.

20. The imaging suite of claim 13 wherein the control and processing system includes:

a means for simultaneously operating the first imaging system and the second imaging system to perform imaging procedures concurrently on first and second subjects supported by first and second patient couches.

21. A method of performing a diagnostic imaging procedure comprising:

a) positioning a subject on a patient table;

b) performing a first imaging procedure on the subject using a first imaging system;

c) transferring the patient table to a second imaging system;

d) performing a second imaging procedure on the subject;

e) generating a first image representation from data generated by the first imaging system;

f) generating a second image representation from data generated by the second imaging system;

g) combining the data representing first image representation and the data representing the second image representation into a combined image representation; and h) displaying at least one of the first image representation, the second image representation, and the combined image representation on at least one monitor.

22. The method of claim 21, wherein step g) includes:

i) combining the data representing first image representation and the data representing the second image representation into the combined image representation based on at least one fiducial associated with the patient table, the at least one fiducial capable of being imaged by the first imaging system and the second imaging system.

23. The method of claim 21, further including:

j) correcting the data representing the second image representation based on the data representing the first image representation.

24. The method of claim 21, wherein the first imaging system includes a computed tomographic (CT) imaging system and the second imaging subsystem includes a nuclear medicine imaging system.

25. The method of claim 21, further including:

i) positioning a second subject on a second patient table;

j) positioning the second subject for imaging with the first imaging system while the first-mentioned subject is positioned for imaging with the second imaging system; and k) performing a third imaging procedure on the second subject with the first imaging system while the second imaging procedure is being performed on the first-mentioned subject with the second imaging system.

26. The method of claim 21, wherein step c) includes:

i) transferring the patient table to a patient transfer system including a translating member along which a patient couch is horizontally translated and a base for moving the translating member into alignment with (i) a first imaging system transfer member along which a patient couch translates, and (ii) a second imaging system transfer member along which a patent couch translates.

* * * * *